US007776084B2

(12) United States Patent  (10) Patent No.: US 7,776,084 B2
Johnson  (45) Date of Patent: Aug. 17, 2010

(54) PROSTHETIC MITRAL HEART VALVE HAVING A CONTOURED SEWING RING

(75) Inventor: Derrick Johnson, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 833 days.

(21) Appl. No.: 11/181,190

(22) Filed: Jul. 13, 2005

(65) Prior Publication Data
US 2007/0016289 A1  Jan. 18, 2007

(51) Int. Cl.
*A61F 2/24* (2006.01)
(52) U.S. Cl. .................. 623/2.19; 623/2.17; 623/2.41
(58) Field of Classification Search ............. 623/2.36, 623/2.4, 2.41, 2.16, 2.37, 2.38, 2.39, 2.17, 623/2.18, 2.12–2.15
See application file for complete search history.

(56) References Cited

U.S. PATENT DOCUMENTS

| 4,451,936 A | | 6/1984 | Carpentier et al. | |
|---|---|---|---|---|
| 5,026,391 A | * | 6/1991 | McQueen et al. | 623/2.33 |
| 5,035,709 A | * | 7/1991 | Wieting et al. | 623/2.2 |
| 5,314,467 A | * | 5/1994 | Shu | 623/2.28 |
| 5,824,069 A | | 10/1998 | Lemole | |
| 5,984,973 A | | 11/1999 | Girard et al. | |
| 6,045,576 A | * | 4/2000 | Starr et al. | 623/2.41 |
| 6,059,826 A | * | 5/2000 | Bokros et al. | 623/2.11 |
| 6,086,612 A | * | 7/2000 | Jansen | 623/2.17 |
| 6,143,025 A | | 11/2000 | Stobie et al. | |

(Continued)

FOREIGN PATENT DOCUMENTS

WO  WO 98/10719  3/1998

OTHER PUBLICATIONS

Medtronic Mosaic Bioprosthesis Specifications Brochure, pp. 1-2, 2001 Medtronic, Inc.

*Primary Examiner*—Corrine M McDermott
*Assistant Examiner*—Suba Ganesan
(74) *Attorney, Agent, or Firm*—Guy L. Cumberbatch, Esq.; Rajiv Yadav, Esq.

(57) ABSTRACT

A prosthetic mitral heart valve including a contoured sewing ring that better matches the mitral valve annulus. The sewing ring includes an inflow end and an outflow end, the outflow and having at least one raised portion. There may be two raised portions located approximately 120° apart from each other and designed to register with two anterior trigones of the mitral valve annulus. The sewing ring may be formed by a suture-permeable annular member surrounded by a fabric covering, the annular member desirably being molded of silicone. The raised portion(s) may gently curve upward to a height of about 2 mm above the adjacent portions of the outflow end of the sewing ring. The sewing ring may also be constructed so as to be more flexible around a posterior aspect than around an anterior aspect to accommodate calcified tissue more commonly found around the posterior annulus. The contoured sewing ring can be combined with various types of heart valve including bioprosthetic and mechanical valves. A bioprosthetic heart valve of the present invention may include a support stent having three outflow commissures alternating with three inflow cusps, with two of the commissures being located at the same place as two raised portions of the sewing ring. A method of implant includes tilting the prosthetic heart valve in the mitral annulus so that a posterior commissure angles away from the ventricular wall and reduces the chance of contact therebetween.

17 Claims, 7 Drawing Sheets

U.S. PATENT DOCUMENTS

| | | |
|---|---|---|
| 6,231,602 B1 * | 5/2001 | Carpentier et al. ......... 623/2.36 |
| 6,558,418 B2 | 5/2003 | Carpentier et al. |
| 6,585,766 B1 | 7/2003 | Huynh et al. |
| 6,719,790 B2 | 4/2004 | Brendzel et al. |
| 2003/0195620 A1 * | 10/2003 | Huynh et al. .............. 623/2.14 |
| 2004/0176839 A1 | 9/2004 | Huynh et al. |
| 2006/0195184 A1 * | 8/2006 | Lane et al. ................. 623/2.38 |

* cited by examiner

PROSTHETIC MITRAL HEART VALVE HAVING A CONTOURED SEWING RING

FIELD OF THE INVENTION

The present invention relates generally to an implantable prosthetic heart valve for the mitral annulus and, more particularly, to a contoured sewing ring for such a prosthetic heart valve.

BACKGROUND OF THE INVENTION

Two primary types of heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,143,025 to Stobie, et al. and U.S. Pat. No. 6,719,790 to Brendzel, et al., the disclosures of which is hereby expressly incorporated by reference. The other is a tissue-type or "bioprosthetic" valve having flexible leaflets supported by a base structure and projecting into the flow stream that function much like those of a natural human heart valve and imitate their natural flexing action to coapt against each other and ensure one-way blood flow. One example of a flexible leaflet valve is disclosed in U.S. Pat. No. 6,585,766 to Huynh, et al., the disclosure of which is hereby expressly incorporated by reference.

In tissue-type valves, a whole xenograft valve (e.g., porcine) or a plurality of xenograft leaflets (e.g., bovine pericardium) typically provide fluid occluding surfaces. Synthetic leaflets have been proposed, and thus the term "flexible leaflet valve" refers to both natural and artificial "tissue-type" valves. Two or more flexible leaflets are mounted within a peripheral support structure that usually includes posts or commissures extending in the outflow direction to mimic natural fibrous commissures in the native annulus. Components of the valve are usually assembled with one or more biocompatible fabric (e.g., Dacron) coverings, and a fabric-covered sewing ring is provided on the inflow end of the peripheral support structure.

In most bioprosthetic-type valves, metallic or polymeric structure provides base support for the flexible leaflets, which extend therefrom. One such support is an elastic "support frame," sometimes called a "wireform" or "stent," which has a plurality (typically three) of large radius cusps supporting the cusp region of the flexible leaflets (i.e., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. The support frame typically describes a conical tube with the commissure tips at the small diameter end. This provides an undulating reference shape to which a fixed edge of each leaflet attaches (via components such as fabric and sutures) much like the natural fibrous skeleton in the aortic annulus. Other "support frame" constructions exhibit sheet-like tubular shapes but still define commissures and cusps on their outflow ends, such as shown in U.S. Pat. No. 5,984,973 to Gerard, et al., the disclosure of which is hereby expressly incorporated by reference.

The most common locations at which prosthetic heart valves are implanted are the aortic and mitral valves associated with the left ventricle, which generates the higher pressures of the two ventricles. The anatomy of the aortic and mitral valves are quite different, with the former being a tri-leaflet structure, and the latter having two dissimilar leaflets. The aortic annulus defines an undulating fibrous structure around substantially a circular ring to support the up-and-down shape of the cusps and commissures of the native leaflets. On the other hand, the mitral annulus has a somewhat fibrous linear anterior aspect across the septum of the heart from the aortic valve, but the posterior aspect, which defines the majority of the annulus, is relatively less fibrous and more muscular. Also, the posterior aspect is nearly oval-shaped such that the mitral annulus presents a malformed "D" shape. Furthermore, the mitral annulus does not exhibit the up-and-down undulating shape around its periphery as does the aortic annulus, and is generally planar, although the anterior aspect thereof is contoured in that it is generally lower at the fibrous trigones and rises up in-between to form something of a saddle shape. The present invention is directed to prosthetic heart valves particularly suited for implant at the mitral annulus.

Figure 1:
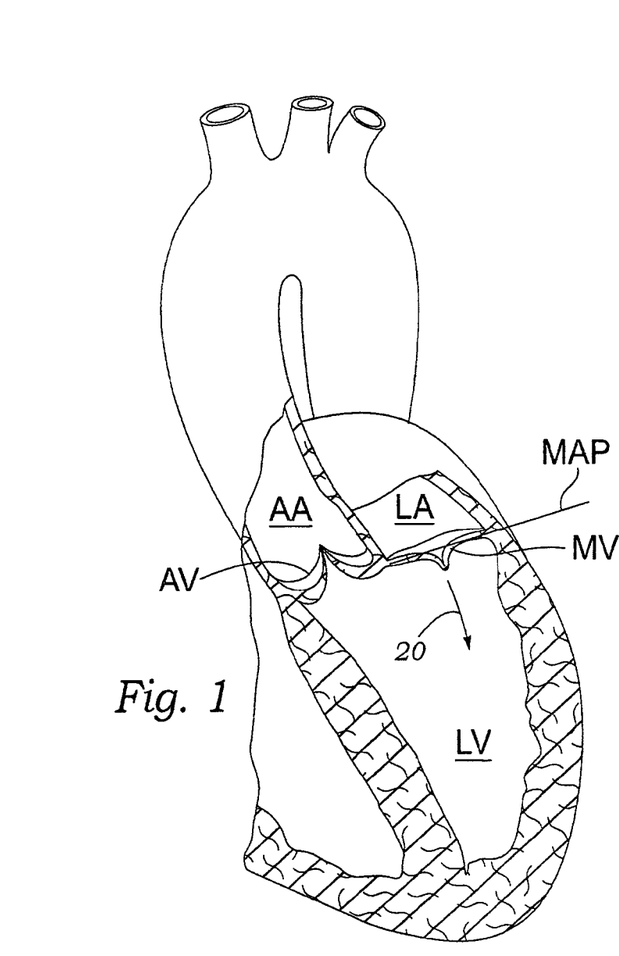
FIG. 1 is a view of the heart illustrating the left ventricle LV and valves associated therewith as seen in partial vertical section along an anterior-posterior plane.

The left ventricle LV and valves associated therewith are depicted in FIG. 1 as seen in vertical cross-section along an anterior-posterior plane. The mitral valve MV controls flow between the left atrium LA and the left ventricle LV, while the aortic valve AV functions between the left ventricle LV and ascending aorta AA. Both the mitral valve and aortic valve include leaflets that extend into the blood flow path and are supported around their peripheries by respective annuluses. For purpose of discussion, the mitral annulus of a normal, healthy heart lies generally in a mitral annulus plane MAP defined perpendicular to the average blood flow direction 20 (see FIG. 1) through the mitral valve MV. Although a typical mitral annulus may be three-dimensional, the mitral annulus plane MAP will be used as a reference plane that extends through the anterior and posterior aspects of the annulus. Papillary muscles are not shown but attach to the lower portion of the interior wall of the left ventricle LV and chordae tendineae extend between and link the papillary muscles and free edges of the anterior and posterior leaflets.

Figure 2:
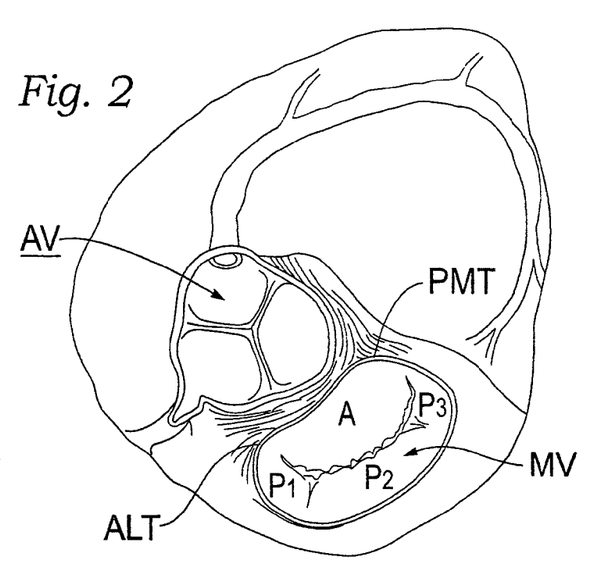
FIG. 2 is a view from above of the aortic and mitral annuluses exposed by removal of the respective atria.
Figure 2A:
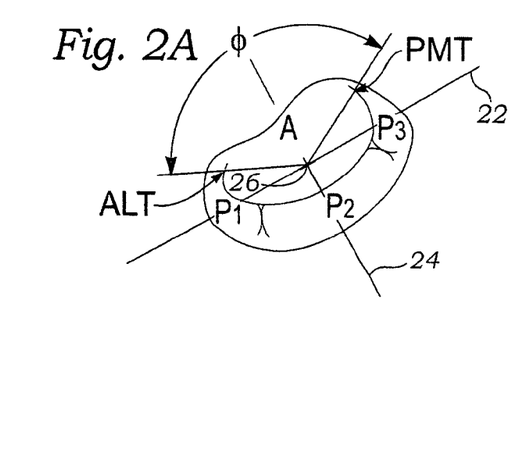
FIG. 2A is a schematic view of the mitral annulus corresponding to be viewed in FIG. 2 and indicating the most prominent anatomical features and nomenclature.

FIG. 2 illustrates the mitral valve from the left atrium as exposed during surgery, while FIG. 2A schematically identifies the commonly identified features in plan view. The average human mitral annular cross-sectional area is 5-11 cm$^2$. The anterior aspect of the mitral annulus forms a part of the "cardiac skeleton" and includes anterolateral ALT and posteriomedial PMT fibrous trigones. The mitral valve MV is a bicuspid valve having a posterior leaflet (separated into three cusps $P_1$, $P_2$, $P_3$) that cooperates or coapts with an anterior leaflet A. The anteriolateral ALT and posteriomedial PMT trigones are indicated at the junction points of the anterior leaflet A and first and third cusps of the posterior leaflet $P_1$, $P_3$, respectively. These junction points are also known as commissures between the leaflets.

As mentioned above, and with reference to FIG. 2A, the mitral annulus has a mal formed "D" shape with the straight portion, or anterior aspect, extending between the anteriolateral ALT and posteriomedial PMT trigones. The longest dimension of the mitral annulus defines a major axis 22 while the shortest dimension defines a minor axis 24. The minor axis 24 generally bisects the anterior leaflet A. Although the mitral annulus is not circular, a center 26 thereof can be defined at the intersection of the major and minor axes 22, 24. Radial lines can be drawn outward from this imaginary center 26 through the anteriolateral ALT and posteriomedial PMT trigones to indicate the angular separation φ therebetween. This angular separation φ varies from patient to patient, but is generally about one-third of the circumference around the mitral annulus, or 120°.

Numerous prosthetic heart valves have been proposed in the art, typically without too much consideration of the unique attributes of the different valve annuluses. In particular, they have been almost no attempts to modify prosthetic valves to better conform to the mitral annulus.

SUMMARY OF THE INVENTION

In accordance with one aspect of the present invention, a sewing ring for a prosthetic heart valve comprises a suture-permeable annular member arranged about an axis defining an inflow-outflow direction. The annular member has a substantially planar inflow end and an outflow end that includes at least one portion that is raised axially with respect to adjacent portions of the outflow end. The axially-raised portion may gently curve upward from the adjacent portions of the outflow end to a height of about 50% of the greatest axial dimension of the annular member. In one embodiment, the largest axial dimension of the annular member is about 4 mm. Preferably, there are two axially-raised portions on the outflow end that are spaced approximately 120° apart.

The annular member may be less flexible at a point mid-way between the axially-raised portions, as located around the shorter distance therebetween, than at a location diametrically opposite that point. The annular member may be constructed of a molded polymer having a plurality of radial walls defining spaces therebetween, wherein there are two spaced apart axially-raised portions on the outflow end. In one embodiment, the radial walls at a point mid-way between the axially-raised portions, as located around the shorter distance therebetween, are thicker than the radial walls at a location diametrically opposite the mid-way point. In another embodiment, the spaces at a point mid-way between the axially-raised portions, as located around the shorter distance therebetween, are smaller than the spaces at a location diametrically opposite the mid-way point. Alternatively, the annular member is constructed of a rolled fabric, there are two spaced apart axially-raised portions on the outflow end, and the fabric is rolled more tightly at a point mid-way between the axially-raised portions, as located around the shorter distance therebetween, than at a location diametrically opposite the mid-way point.

Another aspect of the invention provides a sewing ring for a prosthetic heart valve comprising a suture-permeable annular member arranged about an axis defining an inflow-outflow direction, the annular member having variable compliance around its circumference. The annular member may be constructed of a molded polymer having a plurality of radial walls defining spaces therebetween. In one embodiment the radial walls around one side are thicker than the radial walls around another side, while in an alternative embodiment the spaces around one side are smaller than the spaces around another side. Alternatively, the annular member may be constructed of a polymer fabric, for example a non-woven felt or rolled fabric. In the latter configuration, the fabric is rolled more tightly around one side than another side.

In a particularly preferred embodiment, the sewing ring forms a component of a mitral heart valve for implant at a mitral valve annulus having two trigones spaced about an anterior aspect and a posterior aspect. The annular member then has an anterior side and a posterior side, wherein the annular member is more compliant around its posterior side than around its anterior side. The annular member may be arranged about an axis to define an inflow end and an outflow end, and the outflow end includes two portions generally defining its anterior side that are raised axially with respect to adjacent portions. The two axially-raised portions on the outflow end are desirably spaced approximately 120° apart.

In accordance with a further aspect, a prosthetic mitral heart valve for implant at a mitral valve annulus is provided. The mitral valve annulus features two anterior trigones spaced apart approximately 120°. The heart valve includes a support frame defining an orifice about an axis along an inflow-outflow direction, and a plurality of leaflets mounted for movement on the support frame to provide a one-way valve in the orifice. A sewing ring connects to and is positioned around the support frame for attaching the heart valve to the mitral valve annulus. The sewing ring has an inflow end and an outflow end, and the outflow end includes two axially-raised portions relative to the remainder of the outflow end that are spaced apart so as to register with the two anterior trigones upon implantation.

In the prosthetic mitral heart valve, the support frame may have an undulating shape including three axially-oriented commissures extending toward the outflow direction alternating with three cusps extending toward the inflow direction. In this case, two of the commissures are located adjacent the two axially-raised portions of the sewing ring, and the heart valve includes three flexible leaflets mounted around the undulating shape of the support frame. Alternatively, the support frame has a generally annular configuration, and the heart valve includes two rigid leaflets mounted for pivoting movement within the support frame. In one embodiment, the axially-raised portions gently curve upward from the adjacent portions of the outflow end to a height of about 50% of the greatest axial dimension of the sewing ring. Furthermore, the suture-permeable annular member may have variable compliance around its circumference.

The present invention also provides a method of implanting a prosthetic mitral heart valve at a mitral valve annulus, the annulus featuring two spaced apart anterior trigones. The method includes:

providing a prosthetic mitral heart valve having an outwardly-directed sewing ring for attaching the heart valve to the mitral valve annulus, the sewing ring having an inflow end and an outflow end, wherein the outflow end includes two axially-raised portions relative to the remainder of the outflow end that are spaced apart so as to register with the two anterior trigones; and implanting the prosthetic mitral heart valve in the mitral valve annulus such that the two axially-raised portions are located adjacent the two anterior trigones of the annulus.

Preferably, the sewing ring comprises a suture-permeable annular member, and the step of implanting comprises suturing the sewing ring to the mitral valve annulus. For instance, the sewing ring may be a suture-permeable annular member surrounded by a fabric covering. The prosthetic mitral heart valve may have three axially-oriented commissures extending toward the outflow direction and into the ventricle when the valve is implanted, the first two commissures being located around the heart valve at the same locations as the two axially-raised portions and a third commissure being located equidistant from the first two. In this case, the method includes tilting the prosthetic mitral heart valve at an angle with respect to an annular plane such that the third commissure angles away from the adjacent ventricular wall and reduces the chance of contact therebetween.

In another embodiment, the sewing ring is less flexible at the axially-raised portions than at locations diametrically opposite from the axially-raised portions. The method may be practiced on a mitral annulus featuring a portion that is more calcified than the remainder of the annulus. With such a pathology, the method includes implanting the prosthetic mitral heart valve in the mitral valve annulus such that a relatively more compliant portion of the annular member is located adjacent the portion of the mitral annulus that is more calcified.

Another inventive method of the present invention includes implanting a prosthetic heart valve at a patient's heart valve annulus by first providing a prosthetic heart valve having an outwardly-directed sewing ring for attaching the heart valve to the valve annulus. The sewing ring has a suture-permeable annular member arranged about an axis defining an inflow-outflow direction and which has variable compliance around its circumference. The method includes implanting the prosthetic heart valve in the annulus such that a portion of the annular member that is relatively more compliant than a diametrically opposite portion is located at a predetermined location around the annulus. For instance, the annulus may feature an aspect that is more calcified than the remainder of the annulus, and wherein the step of implanting comprises locating the portion of the annular member that is relatively more compliant adjacent the aspect of the annulus that is more calcified. More particularly, the method may be practiced at a mitral annulus having an anterior aspect and a posterior aspect, and wherein the annular member has an anterior side for attaching to the anterior aspect of the mitral annulus and a posterior side for attaching to the posterior side of the mitral annulus, and the relatively more compliant portion of the annular member is located on the posterior side thereof.

A further understanding of the nature and advantages of the present invention are set forth in the following description and claims, particularly when considered in conjunction with the accompanying drawings in which like parts bear like reference numerals.

DESCRIPTION OF THE PREFERRED EMBODIMENTS

The present invention provides an improved prosthetic heart valve for the mitral annulus. The prosthetic heart valves disclosed herein have a contoured suture ring or sewing ring, sometimes known as a sewing cuff, that better matches the anatomy of the mitral annulus and also positions the valve at an angle relative to the annular plane. The sewing rings have at least one axially-raised portion on their outflow ends that matches up with the anterior aspect of the mitral annulus. In the illustrated embodiment, there are two such axially-raised portions, each corresponding to one of the fibrous trigones of the mitral annulus, while the posterior side of the outflow end is generally planar. It should be understood, however, that the posterior side of the outflow end may also be contoured or have a shape other than an annular plane.

Figures 13, 13A, 13B:
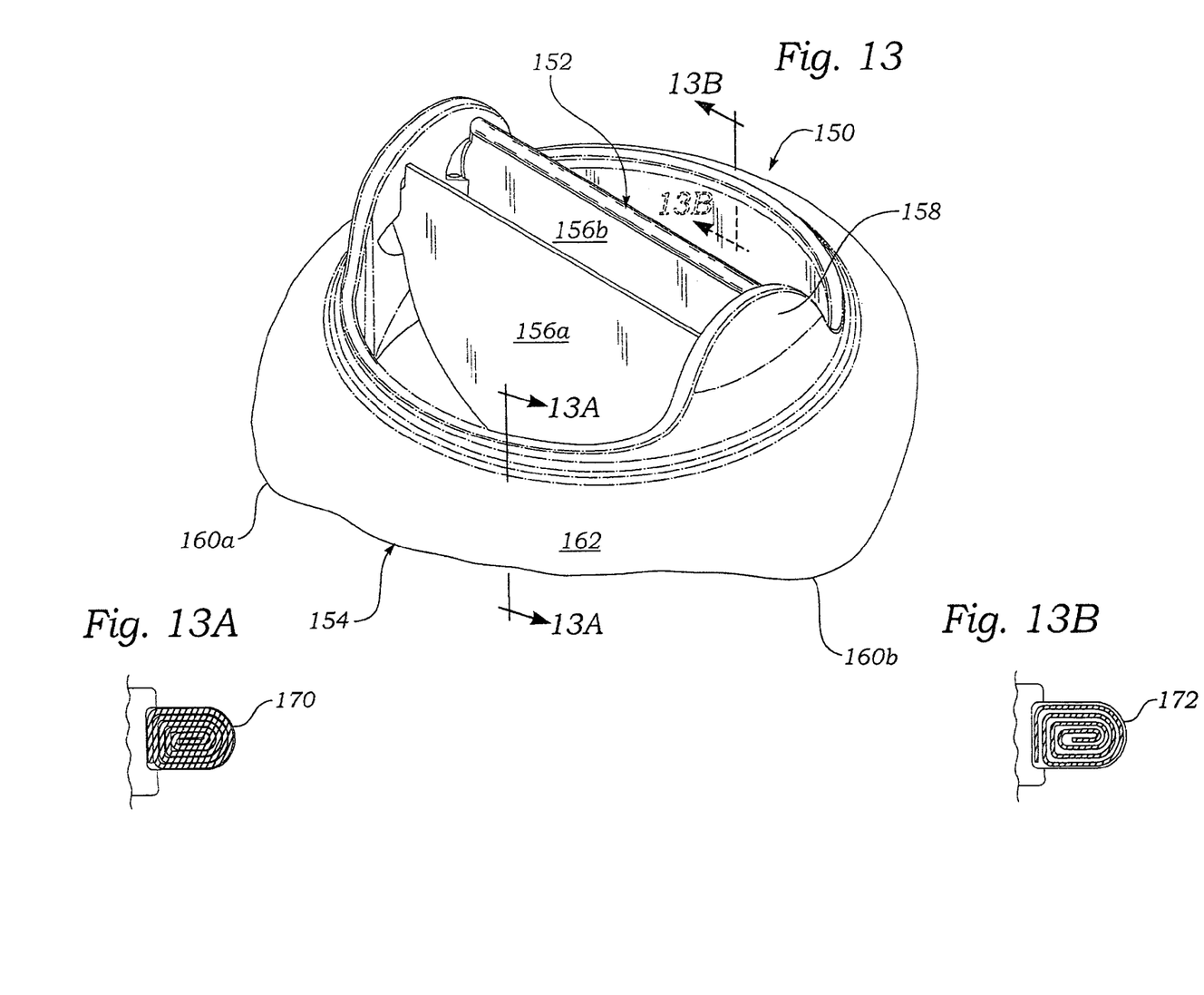
FIG. 13 is a perspective view of an assembled rigid leaflet mitral heart valve of the present invention having a contoured sewing ring.
FIGS. 13A and 13B are radial sectional views through the contoured sewing ring of FIG. 13 taken along respective lines 13A-13A and 13B-13B showing segments of different compliance.

The sewing ring disclosed herein is useful with any sort of prosthetic heart valve, bioprosthetic or mechanical, flexible leaflet or rigid leaflet. The primary illustrated embodiment is a flexible leaflet valve, although a rigid leaflet valve is illustrated in FIG. 13. Those of skill in the art will understand that certain benefits realized by the contoured sewing ring are applicable to all prosthetic mitral heart valves, regardless of occluder construction. For example, although separate flexible leaflets are illustrated, the present invention can also be used with a whole xenograft (e.g., porcine) valve. Moreover, although the term "sewing ring" is used throughout the present application, it should be understood that attachment structures other than sutures may be used to implant the heart valves of the present invention. For example, staples, glue, hooks, barbs, etc., are also contemplated for attaching the sewing ring to the mitral annulus.

As a final word of preface, various angular values are provided for the spacing of the axially-raised portions and other structure of the illustrated sewing rings. These angular values are to some extent dependent on the surrounding mitral anatomy, and to some extent dependent on the occluder structure. For instance, it is often the case that whole porcine valves have three leaflets but commissures that are not equidistantly spaced about the circumference of the valve. A typical distribution of commissures has a spacing of 115°/120°/125°, rather than 120°/120°/120°. So, for example, the slight offset distribution of the commissures of a porcine valve may necessitate a corresponding offset placement of the support structure commissures and axially-raised portions of the sewing ring. Moreover, the native trigones of the mnitral annulus may be spaced apart less than or more than 120°. In this context, therefore, the term "approximately 120°" will be understood to encompass a range of angular values of about 20° on each side, or between 100°-140°.

Figure 3A:
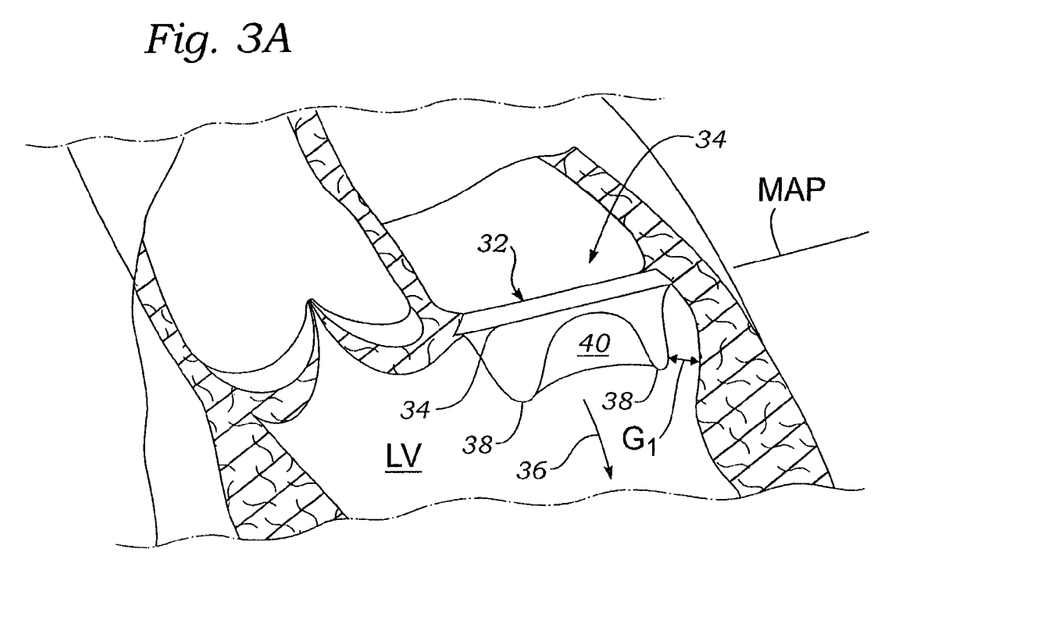
FIG. 3A is a partial vertical section along an anterior-posterior plane illustrating the conventional placement of a prosthetic heart valve of the prior art in a mitral annulus.

Prior to a detailed discussion of an exemplary prosthetic heart valve construction, one of the main advantages of the present invention will be explained with respect to FIGS. 3A and 3B. FIG. 3A shows a prosthetic heart valve 30 having an annular, planar sewing ring 32 implanted in the mitral annulus position. The planar nature of the sewing ring 32, and in particular its outflow end 34, causes the valve 30 to be situated so that the sewing ring is parallel to the mitral annulus plane MAP, described above. A blood flow arrow 36 in the outflow direction extends generally perpendicular to the MAP into the left ventricle LV. The prosthetic heart valve 30 shown has a plurality of outflow commissures 38 supporting flexible leaflets 40 therebetween. As is customary, two of the outflow commissures 38 are positioned adjacent the anterior trigones (not shown) of the mitral annulus, while the third (shown to the right) commissure is on the posterior side and extends into the left ventricle LV close to the inner wall thereof. A gap $G_1$ between this third commissure 38 and the inner wall of the left ventricle LV is indicated.

Figure 3B:
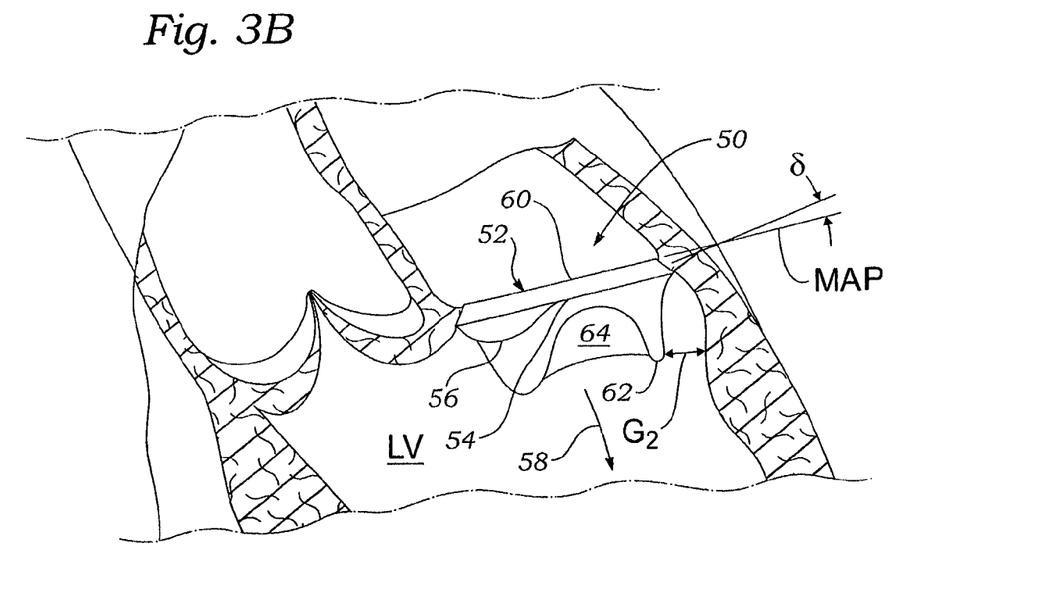
FIG. 3B is a partial vertical section along an anterior-posterior plane illustrating the placement of a prosthetic heart valve of the present invention in a mitral annulus indicating a slightly tilted implant position.

FIG. 3B shows a prosthetic heart valve 50 of the present invention implanted in the mitral annulus position. A sewing ring 52 has a contoured outflow end 54 including a portion 56 that projects axially in the outflow direction with respect to adjacent portions of the outflow end, and which is situated on the anterior side thereof. The presence of the projecting portion 56 lifts that side of the valve 50 and causes it to be situated so that the sewing ring 52 is tilted by an angle δ with respect to the mitral annulus plane MAP. The angle δ is desirably between about 3°-15°, and more preferably is about 7°. A blood flow arrow 58 in the outflow direction extends into the left ventricle LV at an angle that is not quite perpendicular to the MAP.

As in the earlier-described valve 30, the prosthetic heart valve 50 in FIG. 3B has a plurality of outflow commissures 62 supporting flexible leaflets 64 therebetween. Two of the outflow commissures 62 are positioned adjacent the anterior trigones (not shown) of the mitral annulus, while the third (shown to the right) commissure is on the posterior side and extends into the left ventricle LV close to the inner wall thereof. A gap $G_2$ between this third commissure 62 and the inner wall of the left ventricle LV is indicated. The gap $G_2$ is greater than the gap $G_1$ shown in FIG. 3A because of the angle of tilt δ of the valve 50. This increased spacing between the commissure 62 closest to the inner wall of the left ventricle LV helps prevent contact therebetween, and thus reduces the chance of undesirable trauma or abrasion to the left ventricle.

Figure 4:
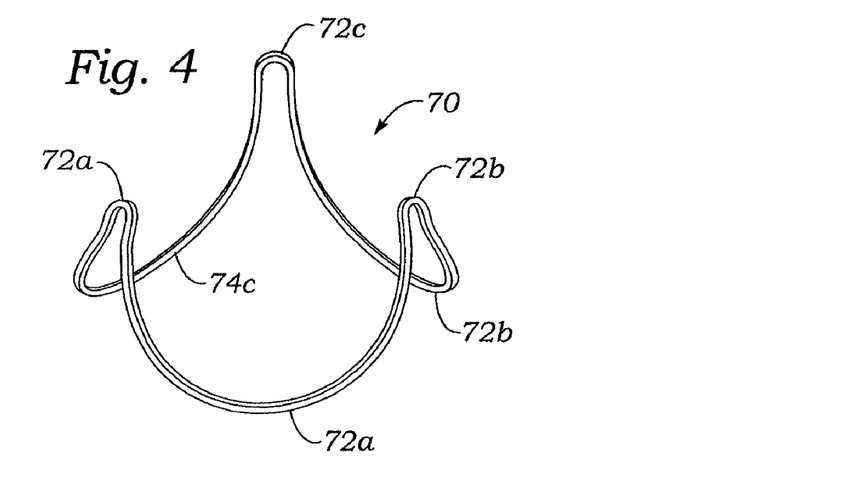
FIG. 4 is a perspective view of an exemplary undulating heart valve support frame.

Now with reference to FIGS. 4-7, the basic construction of the exemplary prosthetic mitral heart valve 50 of the present invention will be described. FIG. 4 illustrates a heart valve support frame 70 that supports the aforementioned leaflets 64 and defines the valve commissures 62 seen in FIG. 3B. The support frame 70 comprises commissures 72a, 72b, 72c on an outflow end alternating with cusps 74a, 74b, 74c on an inflow end. The ends of each pair of adjacent cusps 74 converge asymptotically to form the upstanding commissures 72 that terminate in tips, each extending in a direction opposite to the arcuate cusps and having a relatively smaller radius. If viewed in plan view from above, the peripheral shape of the support frame 70 is substantially tubular with the three commissures 72 being equidistantly spaced apart an angular distance of approximately 120°. The commissures 72 desirably angle slightly radially inwardly from the adjacent cusps 74 so that the support frame 70 defines an approximately conical shape.

Figure 5:
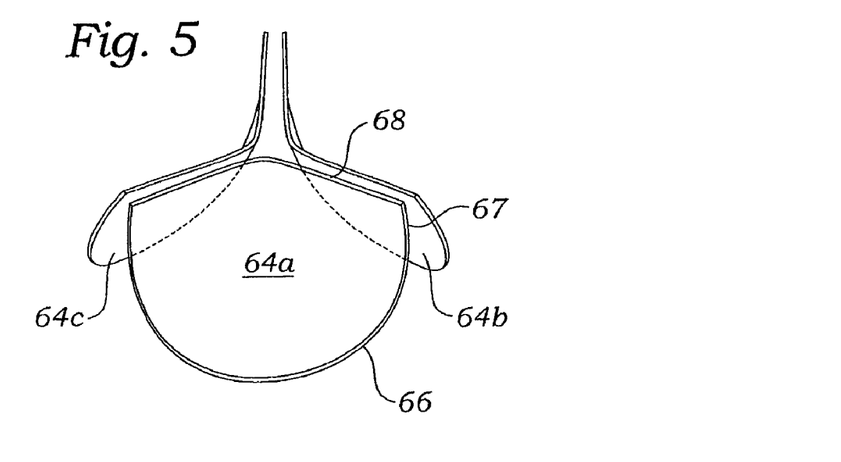
FIG. 5 is a perspective view of three flexible leaflets to be assembled with the support frame of FIG. 4 and used in an exemplary heart valve of the present invention.

The prosthetic valve 50 is a trifoliate valve with three flexible leaflets 64a, 64b, 64c (FIG. 5). Although three leaflets are preferred, and mimic the natural aortic valve, the principles of the present invention can be applied to the construction of a prosthetic valve with two or more flexible leaflets. The leaflets 64 each include an arcuate lower cusp edge 66 terminating in upstanding commissure regions 67, together which define the "peripheral edge" of each leaflet. Each leaflet 64 includes a coapting or free edge 68 opposite the cusp edge 66. In the assembled valve 50, the cusp edges 66 and commissure regions 67 are secured around the periphery of the valve, with the free edges 68 permitted to meet or "coapt" in the middle.

In the exemplary construction of the heart valve 50, the peripheral edges (66, 67) of the leaflets 64 attach to the support frame 70, which therefore defines the shape of the flow orifice and the three-dimensional support structure for the leaflets. The three leaflets 64a, 64b, 64c are arranged in the manner shown in FIG. 5 and the support frame 70 lowered over the top of this subassembly so that juxtaposed peripheral edges of each two adjacent leaflets slot into the axial spaces defined at the commissures 72 of the support frame 70. Although not shown, a fabric covers the support frame 70 and provides an attachment structure to which the leaflets 64 are connected, typically using sutures. As stated above, other valve constructions may not utilize a support frame 70, but can still be combined with a contoured sewing ring 52.

Figure 6:
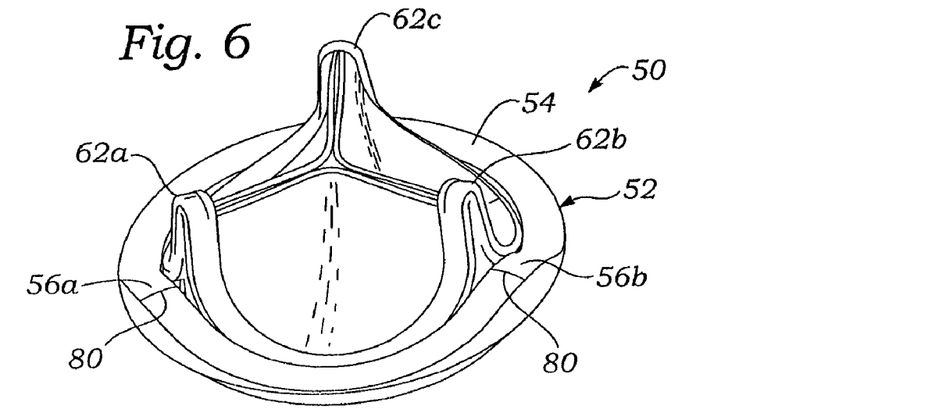
FIG. 6 is a perspective view of an assembled flexible leaflet mitral heart valve of the present invention having a contoured sewing ring.

The assembled prosthetic mitral heart valves 50 is shown in FIG. 6. The near side of the valve 50 is the anterior side, while the opposite side is the posterior side. The aforementioned commissures 62a, 62b, 62c project "upward" in the orientation shown toward the outflow end of the valve 50. The terms "upward" and "axially-raised" are used herein with reference to the orientation of the valve 50 is seen in FIG. 6, with the outflow end being up. Of course, the valve 50 can be flipped over to reverse these directions, as was seen previously in FIGS. 3A and 3B.

The sewing ring 52 surrounds the fabric-covered cusps 74 of the support frame 70 and is attached thereto with a line of stitching or other such means. As mentioned, the outflow end 54 of the sewing ring 52 includes at least one portion 56 that projects axially in the outflow direction with respect to adjacent portions of the sewing ring outflow end. In the illustrated embodiment, there are two such axially-raised portions 56 spaced approximately 120° apart and positioned radially outward from two of the commissures 62a, 62b. Radial lines 80 drawn across the outflow end 54 denote the apices of both of these axially-raised portions 56a, 56b, and may be included as location markers on the exterior of the sewing ring 52.

Figure 7A:
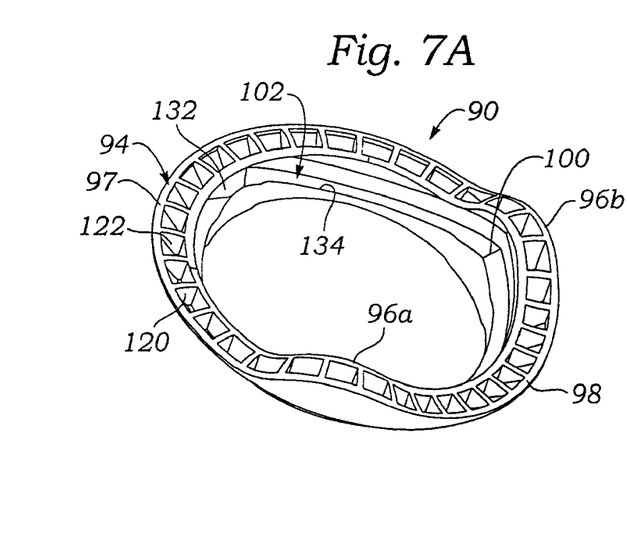
FIGS. 7A and 7B are outflow and inflow end perspective views, respectively, of an exemplary annular member of a sewing ring of the present invention.
Figure 7B:
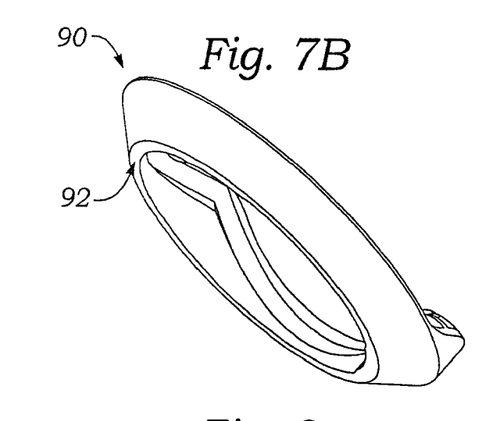

A preferred construction of the sewing ring 52 includes a suture-permeable annular member 90 as seen in FIGS. 7A and 7B covered with fabric. The annular member 90 has a substantially planar inflow end 92 and a contoured outflow end 94 that includes two axially-raised portions 96a, 96b. Preferably, the annular member 90 is molded from a suture-permeable, biocompatible polymer such as silicone and has a plurality of walls defining spaces or cells therebetween. As seen in FIG. 7A, the spaces open to the outflow end 94, while FIG. 7B illustrates a substantially continuous, closed inflow end 92.

Figure 8:
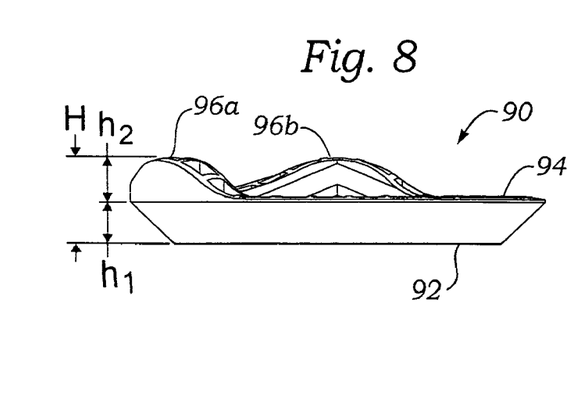
FIG. 8 is an elevational view of one side of the sewing ring annular member.
Figure 9:
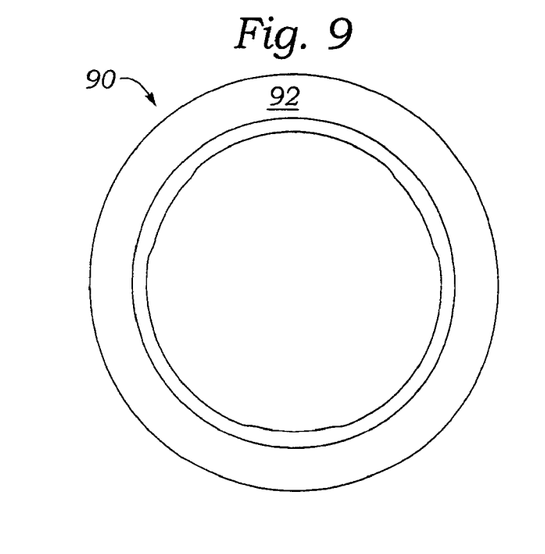
FIG. 9 is a plan view of the inflow end of the annular member.

FIGS. 8-12 describes the exemplary structural details of the suture-permeable annular member 90. FIG. 8 shows the annular member 90 in elevational view and the axial heights of the raised portions 96a, 96b relative to the remainder of the outflow end 94. The total axial dimension of the annular member 90 is shown to the left as H. The nominal height $h_1$ of the majority of the annular member is approximately one half of the total annular member height H, as is the additional height $h_2$ of the axially-raised portions 96a, 96b. Stated another way, the axially-raised portions 96a, 96b rise upward from the adjacent portions of the outflow end 94 to a height of about 50% of the greatest axial dimension of the annular member 90. In accordance with one embodiment, the axially-raised portions 96a, 96b rise upward a height $h_2$ of about 2 mm from the adjacent portions of the outflow end 94, and the total height H of the annular member 90 is about 4 mm.

Figure 11:
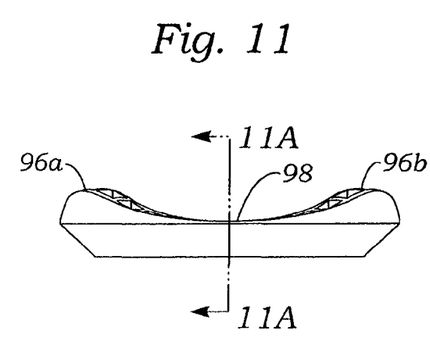
FIG. 11 is an elevational view of another side of the annular member.
Figure 12:
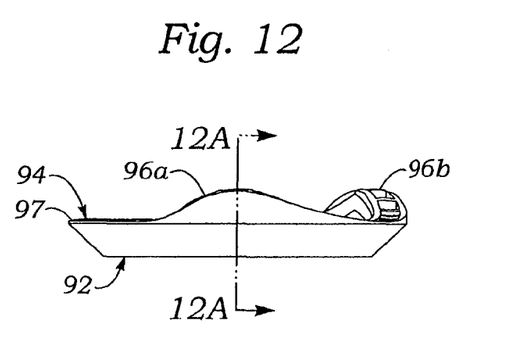
FIG. 12 is an elevational view of a still further side of the annular member.

In a preferred embodiment, the axially-raised portions 96a, 96b gently curve upward from the adjacent portions of the outflow end to their apices and are substantially symmetric about a circumferential midpoint. As mentioned above, the raised portions 96a, 96b of the annular member 90 are provided on an anterior side thereof. The posterior side 97 of the outflow end 94 is substantially planar and parallel to the inflow end 92, as seen in FIG. 8. FIG. 11 illustrates the symmetry between the two raised portions 96a, 96b with a trough 98 centered therebetween. FIG. 12 shows the raised portions 96a, 96b as they curve down away from each other to the substantially planar posterior side 97. As defined herein, the raised portions 96a, 96b are elevated with respect to "adjacent portions" which are defined in one direction by the generally planar posterior side 97 and in the other direction by the trough 98 on the anterior side.

With reference now to the plan view of the outflow end 94 in FIG. 10, short radial lines indicate apices 100 at the circumferential midpoints of the raised portions 96a, 96b along an inner ledge 102 (more fully described below). An overall plane of symmetry 104 is drawn through the annular member 90 that bisects the two apices 100 and passes through the center thereof. This plan view illustrates the symmetric circumferential distribution of the apices 100 about the plane 104. Preferably, the apices 100 are located approximately 60° from the plane of symmetry, or approximately 120° from each other, as measured by the shortest distance around the annular member 90.

Figure 10:
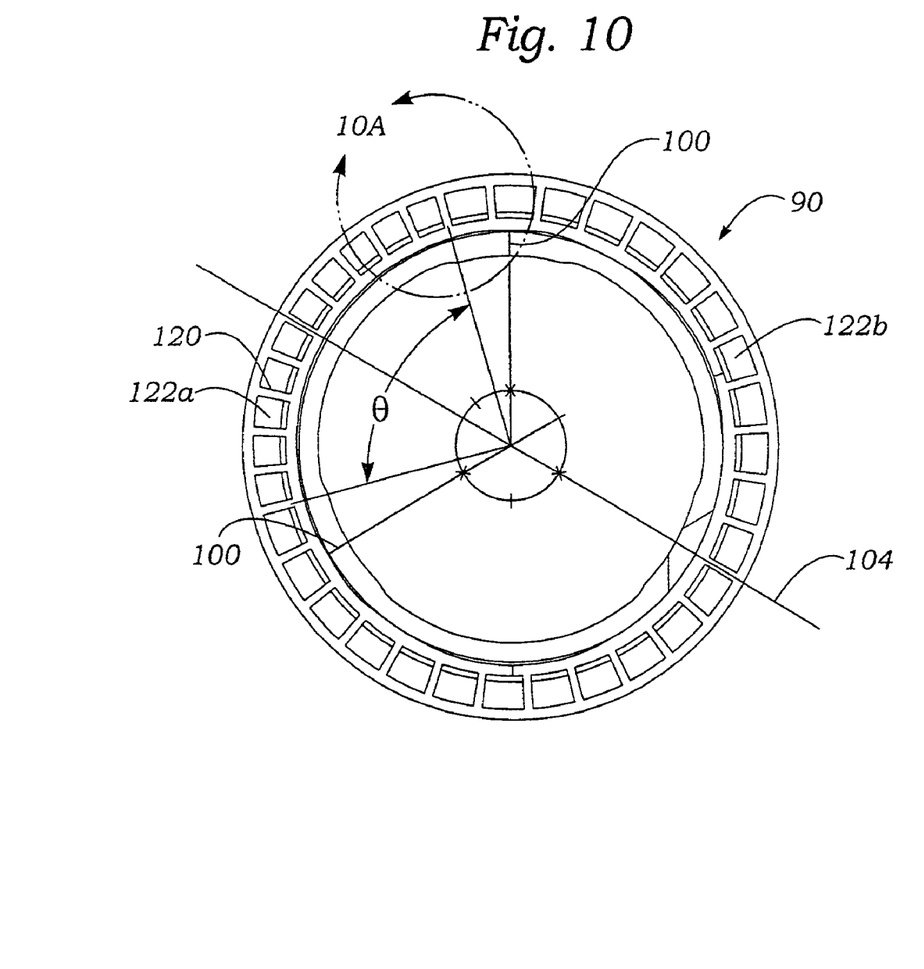
FIG. 10 is a plan view of the outflow end of the annular member showing a plurality of radial walls defining varying sized spaces therebetween.
Figure 12A:
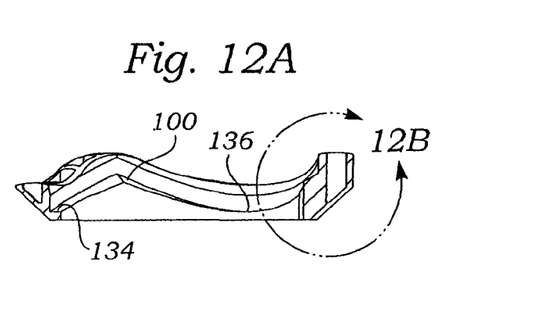
FIG. 12A is a radial cross-section taken therethrough.
Figure 12B:
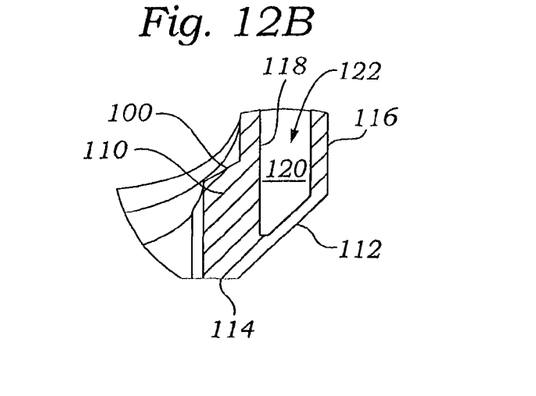
FIG. 12B is an enlarged view of the radial cross-section through the annular member.

The annular member 90 as seen in FIGS. 10-12 comprises a plurality of walls defining spaces or cells therebetween. As seen best in FIG. 12B, a relatively thick continuous inner wall 110 extends 360° around the annular member 90, as does a continuous conical wall 112 that angles radially outward and in the outflow direction from the inner wall 110. As seen from the bottom in FIG. 9, and in cross-section in FIG. 11, a bottom surface 114 of the inner wall 110 and the conical wall 112 together define a continuous or solid wall of the annular member 90 that faces in the inflow direction. FIG. 12B is a radial sectional view through one of the raised portions 96a illustrating an outer partial tubular wall segment 116 that projects upward from the outermost rim of the conical wall 112. An inner partial tubular wall segment 118 projects upward from the inner wall 110 also in the area of the raised portions 96. A plurality of radial walls 120 connect the inner wall 110, conical wall 112, and outer wall segment 116, and define therebetween a plurality of cells or spaces 122 open to the outflow end 94. The combined shape of the upwardly projecting wall segment 116, 118 and radial walls 120 therebetween define the raised portions 96a, 96b of the annular member 90.

As seen in FIG. 10, the radial walls 120 and spaces 122 therebetween are distributed around the entire circumference of the annular member 90. As seen also in FIG. 7A, the spaces 122 open to the outflow end 94 of the annular member 90. Ultimately, the sewing ring 52 will be encompassed by a fabric, as seen in FIG. 6, and thus the spaces 122 are not visible in the finished valve. The spaces 122 provide a "waffle" structure to the annular member 90 and render it highly compliant. Desirably, the annular member 90 is molded from a suitable biocompatible polymer such as silicone or polyurethane, and the spaces 122 facilitate formation of the walls 110-120 and permit easy release of the mold parts.

Figure 10A:
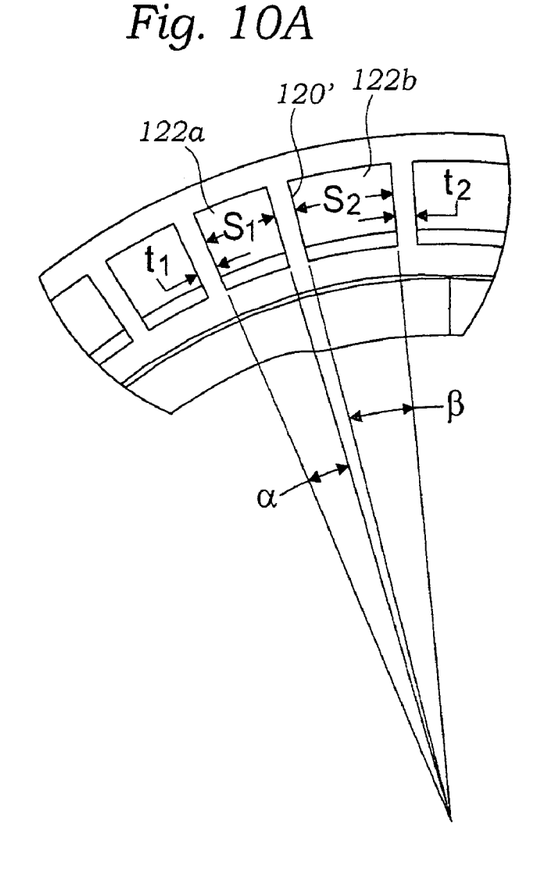
FIG. 10A is an enlarged view of a portion of the outflow end of the annular member detailing the differently sized spaces.

FIGS. 10 and 10A also illustrate a preferred construction for varying the compliance of the annular member 90 around its circumference. As mentioned above, the apices 100 of the raised portions 96a, 96b are spaced apart approximately 120°. Within this arc the walls 120 are separated by a smaller distance than at a location opposite from this arc such that the spaces 122 are smaller and the annular member 90 stiffer. More desirably, an angle $\theta$ is shown bisected by the plane of symmetry 104 and thus positioned centrally between the apices 100. The lines forming the angle $\theta$ extend through radial walls 120 that define a transition between differently sized spaces 122. In one embodiment, the angle $\theta=90°$, but $\theta$ desirably ranges between 80-120°.

Enlarged FIG. 10A best illustrates the transition between differently sized spaces 122. A radial wall 120' separates a first space 122a from a second space 122b. The first space 122a spans an angle $\alpha$, while the second space 122b spans an angle $\beta$, where $\beta > \alpha$. This angular relationship results in arc dimensions of $S_1$ and $S_2$, respectively, as taken at a nominal radius through a radial midpoint of each of the spaces 122a, 122b, which dimensions depend on the size of the annular member 90. It should be understood that heart valves are produced in various sizes, typically between 21-35 mm in outside diameter, therefore the sewing ring 52 and annular member 90 will be provided in varying sizes. It will be understood that, everything else being the same, the annular member 90 is more compliant where the spaces 122b are larger.

The following table provides exemplary dimensions for an annular member 90 sized for a 27 mm prosthetic valve, wherein each space 122 is termed a "cell." In this example, the cell walls 120 are all of equal thickness.

| DESCRIPTION | VARIABLE | DIMENSION |
| --- | --- | --- |
| Inner Radius of Cell | $R_1$ | 0.633 in |
| Outer Radius of Cell | $R_2$ | 0.710 in |
| Average Radius | $R_{Center}$ | 0.672 in |
| Small Cell (122a) Angle | $\alpha$ | 6.88° ± 5° |
| Large Cell (122b) Angle | $\beta$ | 9.30° ± 5° |
| Small Cell Arc Length of Center Radius | $S_1$ | 0.081 ± .059 in |
| Large Cell Arc Length of Center Radius | $S_2$ | 0.109 ± .059 in |
| Small Cell Wall Angle | $\lambda$ | 2.00° ± 1° |
| Large Cell Wall Angle | $\mu$ | 2.00° ± 1° |
| Small Cell Wall Arc Length of Center Radius | $t_1$ | 0.023 ± 0.01 in |
| Large Cell Wall Arc Length of Center Radius | $t_2$ | 0.023 ± 0.01 in |

As mentioned above, the arc between the raised portions 96 delineated by the apices 100 in FIG. 10 subtends an angular section of the member 90 that is intended to be positioned at the anterior aspect of the mitral annulus. Because the spaces 122a are smaller generally between the apices 100 (or at least within the angle $\theta$), the anterior side of the member 90 and sewing ring 52 is thus less compliant than the posterior side 97. The more compliant, less stiff posterior side 97 is desirable so that the sewing ring 52 can more easily conform to often calcified tissue on the posterior aspect of the mitral annulus. In the preferred embodiment, however, the sewing ring is less flexible at a point mid-way between the axially-raised portions 96, as located around the shorter distance therebetween, than at a location diametrically opposite the mid-way point.

Those of skill in the art will understand that designing the annular member 90 to be more compliant around its posterior side 97 is just one possible configuration motivated by a particular understanding of the character of the tissue around the mitral annulus, in this case a more calcified posterior aspect. Of course, the compliance characteristics of the ring around its circumference can be customized in other ways such that it is more compliant around the anterior side, for example. In general, the present invention contemplates a sewing ring 52 that has variable compliance around its circumference. For example, one arrangement contemplated is to have alternating large and small cells, in which case the regions of alternating high and low compliance are smaller and more frequent, as opposed to being segregated on one side or the other.

Still with reference to FIG. 10A, the compliance of the sewing ring 52, or more particularly the annular member 90, around its circumference can be varied in other ways besides varying the spacing between the walls 120. For example, the walls 120 themselves can be provided in different thicknesses, such as by making the angles λ and μ in the above table unequal. In the less compliant (stiffer) section indicated to the left of the transition wall 120', the radial walls 120 may have a thickness $t_1$, while to the right of the transition wall the radial walls 120 may have a thickness $t_2$, with $t_2 < t_1$ (in angular terms, λ>μ). By making the radial walls 120 thinner around the posterior side 97 of the annular member 90, it is also more compliant in that region. Furthermore, varying the thicknesses of the radial walls 120 may be combined with varying the dimensions of the spaces 122 to create an even greater difference in flexibility. Moreover, the distinct transition at the wall 120' between the areas of unequal flexibility may be replaced with a more gradual transition.

It should also be understood that the construction of the sewing ring may be other than that shown in FIGS. 7-12. There are certain distinct advantages to constructing the sewing ring with a molded silicone "waffle," as illustrated, but the overall benefit of providing axially-raised portions on the anterior side of the outflow end of the sewing ring and varying flexibility can be attained with a variety of constructions. For example, other polymers (e.g., polyurethane) can be used to form the waffle structure, or the particular arrangement of the walls and spaces may be modified. Certain biocompatible fabrics may also be used to form a sewing ring, such as non-woven, non-compressed polyester or polyethylene terepthalate. Indeed, one particularly useful method for forming sewing rings is to roll or fold such fabric into the contour needed and then heat set the fabric to the desired shape. Such roll or folded cloth or fabric can also be manufactured to have varying compliance around the circumference of the sewing ring. For example, by rolling such fabric more tightly around the anterior side of the sewing ring, it can be made stiffer than the posterior side 97. Therefore, unless particularly claimed, it should be understood that the invention is not limited to a molded "waffle-like" polymer inner member for the sewing ring.

Figure 11A:
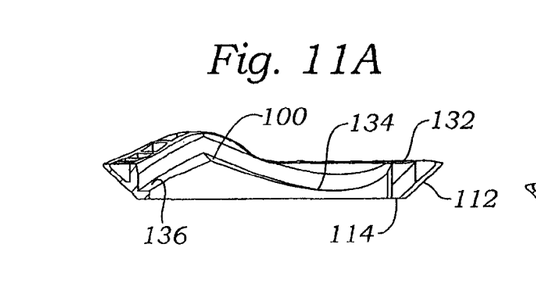
FIG. 11A is a radial cross-section taken therethrough.

Certain other structural details of the exemplary annular member 90 that facilitate its assembly with the other parts of a flexible leaflet heart valve are shown in the perspective views of FIGS. 7A and 7B, and in the detailed views of FIGS. 11-12. More particularly, FIG. 7A best illustrates the inner ledge 102 on which are supported the three cusps 74a, 74b, 74c (FIG. 4) of the support frame 70 in the assembled valve 50. The inner ledge 102 is also seen in sectional views in FIGS. 11, 12A, and 12B, and transitions from a horizontal platform 132 at the midpoint of the posterior side 97 thereof, to a small horizontal flange 134, and from there upward to the apices 100 at the raised portions 96a, 96b. The ledge 102 descends to another small horizontal flange 136 at the midpoint of the anterior side, halfway between the apices 100. As seen in FIG. 11A, the ledge 102 is substantially horizontal at its lower extremities, and transitions to have a slightly inward and downward angle as it rises axially upward, culminating in the apices 100 as seen in the enlarged view of FIG. 12B.

The assembly construction of the valve 50 essentially comprises covering the support frame 70 shown in FIG. 4 with a fabric having a flange extending outwardly therefrom. The annular member 90 is also covered with a fabric, and the peripheral edges of the leaflets 64 are sandwiched between and fastened to the fabric coverings of the support frame 70 and annular member 90. As mentioned, the cusps 74 of the support frame 70 conform closely to the contours of the inner ledge 102 and in suturing the various elements together the assembly is made relatively dimensionally stable. That is, the support frame 70 is prevented from migrating in an inflow direction through the annular member 90 by the inner ledge 102. More complete discussions of these fabrication techniques are provided in U.S. Pat. No. 6,585,766 to Huynh, et al., and in U.S. application Ser. No. 11/039,522, and entitled ANATOMICALLY APPROXIMATE PROSTHETIC MITRAL HEART VALVE, the disclosures which are expressly incorporated herein by reference.

The contours of the raised portions 96a, 96b are also important to enhance contact between the sewing ring 52 and the surrounding mitral annulus, as well as provide the aforementioned benefits of lifting the anterior side upward so as to tilt the entire valve away from the left ventricle wall. As seen best in the elevational views of FIGS. 11 and 12, each of the raised portions 96a, 96b defines a smooth curvature with no abrupt corners. FIG. 11 illustrates the symmetry between the two raised portions 96a, 96b wherein the anterior side of the outflow end 94 comprises a gradual reduction in height from the raised portions to the trough 98. The trough 98 has approximately the same height as the opposite side of the outflow end 94 of the annular member 90, as seen on the left side of FIG. 12. The circumferential arc around which the axial dimension of the annular member 90 changes from the highest point of the raised portions 96a, 96b to the lowest point of the trough 98 is therefore approximately 60°. On the other hand, with reference to FIG. 12, the transition between the highest point of the raised portions 96a, 96b and the substantially planar posterior side 97 is less gradual, although still smooth. The circumferential arc distance between the top of the raised portions 96a, 96b and the planar posterior side 97 of the outflow end 94 is about 20°.

Now with reference to FIG. 13, an alternative prosthetic heart valve 150 of the present invention comprises a mechanical valve member 152 coupled with a contoured sewing ring 154 of the present invention. The valve member 152 includes rigid leaflets 156a, 156b that are coupled for pivotal movement within a surrounding support frame 158. The sewing ring 154 attaches around the periphery of the support frame 158. In this view, the inflow end of the valve member 152 is up, while the outflow end is down. Two raised portions 160a, 160b are provided in the sewing ring 154, much like the earlier-described flexible leaflet embodiment. The raised portions 160a, 160b are desirably circumferentially spaced apart on the anterior side of the sewing ring 154 to correspond to the native trigones (typically about 120°). It should be noted that the mechanical valve member 152 is typically rotatable within the surrounding support frame 158 and thus the orientation shown relative to the contoured sewing ring 154 should not be considered limiting. The sewing ring 154 has a fabric exterior 162 which may cover an inner waffle-like annular member as described above, or may be simply an outer layer of a rolled or folded fabric construction.

FIGS. 13A and 13B are radial sectional views through the contoured sewing ring 154 of FIG. 13 taken along respective lines 13A-13A and 13B-13B showing segments of differential compliance. In this embodiment, the sewing ring 154 is made with a rolled fabric construction, and the varying compliance is obtained by more tightly rolling the fabric in one side 170 than in another side 172. Desirably, the more tightly wound and thus less compliant side 170 is on the anterior side of a mitral valve 150 and the more loosely wound and thus more compliant side 172 is on the posterior side. In another commercial construction, non-woven polymer fabric or polyester felt, something like pillow stuffing, is used. In the latter configuration, the polyester felt may be more tightly packed around one side of the sewing ring 154 relative to another.

It will also be appreciated by those of skill in the relevant art that various changes may be made to the examples and embodiments of the invention described in this provisional application, without departing from the intended scope of the invention. The particular embodiments of the invention described herein are thus to be understood as examples of the broader inventive concept disclosed in this application.

What is claimed is:

1. A prosthetic mitral heart valve for implant at a mitral valve annulus, the annulus featuring two anterior trigones spaced apart approximately 120°, comprising:
a support frame defining an orifice about an axis along an inflow-outflow direction;
a plurality of leaflets mounted for movement on the support frame to provide a one-way valve in the orifice; and
a sewing ring connected to and positioned around the support frame for attaching the heart valve to the mitral valve annulus, the sewing ring having an inflow end and an outflow end, wherein the outflow end includes exactly two axially-raised portions relative to the remainder of the outflow end that are spaced apart so as to register with the two anterior trigones upon implantation, the two axially-raised portions both extending the full radial extent of the sewing ring,
wherein the support frame has an undulating shape including three axially-oriented commissures extending toward the outflow direction alternating with three cusps extending toward the inflow direction, two of the commissures being located adjacent the two axially-raised portions of the sewing ring, and the heart valve includes three flexible leaflets mounted around the undulating shape of the support frame.

2. The heart valve of claim 1, wherein the axially-raised portions gently curve upward from the adjacent portions of the outflow end to a height of about 50% of the greatest axial dimension of the sewing ring.

3. The heart valve of claim 1, wherein the suture-permeable annular member has variable compliance around its circumference.

4. The heart valve of claim 3, wherein the sewing ring is less flexible at a point mid-way between the axially-raised portions, as located around the shorter distance therebetween, than at a location diametrically opposite the mid-way point.

5. The heart valve of claim 4, wherein the sewing ring comprises a suture-permeable annular member surrounded by a fabric covering, the annular member having a plurality of radial walls defining spaces therebetween, and wherein the radial walls at a point mid-way between the axially-raised portions, as located around the shorter distance therebetween, are thicker than the radial walls at a location diametrically opposite the mid-way point.

6. The heart valve of claim 4, wherein the sewing ring comprises a suture-permeable annular member surrounded by a fabric covering, the annular member having a plurality of walls defining spaces therebetween, and wherein the spaces at a point mid-way between the axially-raised portions, as located around the shorter distance therebetween, are smaller than the spaces at a location diametrically opposite the mid-way point.

7. The heart valve of claim 1, wherein the sewing ring comprises a rolled fabric, wherein the fabric is rolled more tightly at a point mid-way between the axially-raised portions, as located around the shorter distance therebetween, than at a location diametrically opposite the mid-way point.

8. A prosthetic mitral heart valve for implant at a mitral valve annulus, the annulus featuring two anterior trigones spaced apart approximately 120°, comprising:
a support frame defining an orifice about an axis along an inflow-outflow direction;
a plurality of leaflets mounted for movement on the support frame to provide a one-way valve in the orifice; and
a sewing ring connected to and positioned around the support frame for attaching the heart valve to the mitral valve annulus, the sewing ring having an inflow end and an outflow end, wherein the outflow end includes two axially-raised portions relative to the remainder of the outflow end that are spaced apart so as to register with the two anterior trigones upon implantation, and
wherein the sewing ring comprises a suture-permeable annular member surrounded by a fabric covering, the annular member having a plurality of walls defining spaces therebetween, and wherein the spaces at a point mid-way between the axially-raised portions, as located around the shorter distance therebetween, are smaller than the spaces at a location diametrically opposite the mid-way point, such that the sewing ring is less flexible at the mid-way point between the axially-raised portions than at the diametrically opposite location.

9. The heart valve of claim 8, wherein the support frame has an undulating shape including three axially-oriented commissures extending toward the outflow direction alternating with three cusps extending toward the inflow direction, two of the commissures being located adjacent the two axially-raised portions of the sewing ring, and the heart valve includes three flexible leaflets mounted around the undulating shape of the support frame.

10. The heart valve of claim 8, wherein the support frame has a generally annular configuration, and the heart valve includes two rigid leaflets mounted for pivoting movement within the support frame.

11. The heart valve of claim 8, wherein the axially-raised portions gently curve upward from the adjacent portions of the outflow end to a height of about 50% of the greatest axial dimension of the sewing ring.

12. The heart valve of claim 8, wherein the radial walls of the annular member at the mid-way point between the axially-raised portions are thicker than the radial walls at the diametrically opposite location.

13. The heart valve of claim 8, wherein the spaces between the axially-raised portions, as located around the shorter distance therebetween, are all smaller than the spaces around the rest of the annular member.

14. A prosthetic mitral heart valve for implant at a mitral valve annulus, the annulus featuring two anterior trigones spaced apart approximately 120°, comprising:

a support frame defining an orifice about an axis along an inflow-outflow direction;

a plurality of leaflets mounted for movement on the support frame to provide a one-way valve in the orifice; and a sewing ring connected to and positioned around the support frame for attaching the heart valve to the mitral valve annulus, the sewing ring having an inflow end and an outflow end, wherein the outflow end includes two axially-raised portions relative to the remainder of the outflow end that are spaced apart so as to register with the two anterior trigones upon implantation, and wherein the sewing ring comprises a suture-permeable annular member surrounded by a fabric covering, the annular member having a plurality of radial walls defining spaces therebetween, and wherein the radial walls at a point mid-way between the axially-raised portions, as located around the shorter distance therebetween, are thicker than the radial walls at a location diametrically opposite the mid-way point, such that the sewing ring is less flexible at the mid-way point between the axially-raised portions than at the diametrically opposite location.

15. The heart valve of claim 14, wherein the support frame has an undulating shape including three axially-oriented commissures extending toward the outflow direction alternating with three cusps extending toward the inflow direction, two of the commissures being located adjacent the two axially-raised portions of the sewing ring, and the heart valve includes three flexible leaflets mounted around the undulating shape of the support frame.

16. The heart valve of claim 14, wherein the support frame has a generally annular configuration, and the heart valve includes two rigid leaflets mounted for pivoting movement within the support frame.

17. The heart valve of claim 14, wherein the axially-raised portions gently curve upward from the adjacent portions of the outflow end to a height of about 50% of the greatest axial dimension of the sewing ring.

* * * * *